United States Patent [19]

Dean, Jr. et al.

[11] Patent Number: 4,978,616
[45] Date of Patent: Dec. 18, 1990

[54] FLUIDIZED CELL CULTIVATION PROCESS

[75] Inventors: Robert C. Dean, Jr., Norwich; Peter V. Grela, Windsor, both of Vt.; Subhash B. Karkare, Thousand Oaks, Calif.; Peter W. Runstadler, Jr., Hanover, N.H.

[73] Assignee: Verax Corporation, Lebanon, N.H.

[21] Appl. No.: 92,599

[22] Filed: Sep. 3, 1987

Related U.S. Application Data

[63] Continuation-in-part of Ser. No. 932,104, Nov. 18, 1986, abandoned, which is a continuation-in-part of Ser. No. 706,872, Feb. 28, 1985, abandoned, which is a continuation-in-part of Ser. No. 527,390, Aug. 29, 1983, abandoned.

[51] Int. Cl.$^5$ .................... C12P 21/00; C12N 1/00; C12N 5/02
[52] U.S. Cl. .................... 435/70.3; 435/71.1; 435/240.24; 435/243; 435/813; 435/819
[58] Field of Search ........... 435/240.1, 240.23, 240.24, 435/813, 819, 41, 70.1–71.3, 243; 210/617, 616, 150, 261, 262; 261/114 A, 124

[56] References Cited

U.S. PATENT DOCUMENTS

| | | |
|---|---|---|
| 2,244,902 | 6/1941 | Stich . |
| 2,705,136 | 3/1955 | Glitsch . |
| 2,819,049 | 1/1958 | Manning et al. . |
| 2,856,273 | 10/1958 | Beber et al. . |
| 3,114,677 | 7/1961 | Stich . |
| 3,528,889 | 9/1970 | Portno . |
| 3,928,143 | 12/1975 | Coughlin et al. . |
| 4,001,090 | 1/1977 | Kalina ............................ 435/813 X |
| 4,016,044 | 4/1977 | Fresnel et al. . |
| 4,032,407 | 6/1977 | Scott et al. . |
| 4,045,184 | 8/1977 | Haralampiev et al. . |
| 4,048,018 | 9/1977 | Coughlin et al. . |
| 4,127,447 | 11/1978 | Griffith et al. . |
| 4,138,290 | 2/1979 | McMullen et al. . |
| 4,153,510 | 5/1979 | Messing et al. . |
| 4,167,450 | 9/1979 | Chesbro et al. ................ 435/813 X |
| 4,189,534 | 2/1980 | Levine et al. . |
| 4,209,591 | 6/1980 | Hendriks . |
| 4,256,839 | 3/1981 | Solomons et al. . |
| 4,337,315 | 6/1982 | Fukushima et al. . |
| 4,397,953 | 8/1983 | Guazzone et al. . |
| 4,415,668 | 11/1983 | Siegel . |
| 4,519,959 | 5/1985 | Takeuchi et al. . |

FOREIGN PATENT DOCUMENTS

| | | |
|---|---|---|
| 2606402 | 8/1977 | Fed. Rep. of Germany ...... 435/311 |
| 323145 | 2/1972 | U.S.S.R. . |
| 2059436 | 4/1981 | United Kingdom . |
| 2082164A | 3/1982 | United Kingdom . |

OTHER PUBLICATIONS

Aiba, Humphrey, Millis, "Biochemical Engineering" Academic Press, 1973, pp. 47–49, *S. Cerevisiae.*
V. Krumphanzl (editor), "Overproduction of Microbial Products", Academic Press, 1982, pp. 216–219.
S. Fazekas de St. Groth, "Automated Production of Monoclonal Antibodies in a Cytostat", Journal of Immunological Methods, vol. 57, pp. 121–136 (1983).
Boraston et al., "Growth and Oxygen Requirements of Antibody Producing Mouse hybridoma Cells in Suspension Culture", 5th General Meeting of E.S.A.C.T. Copenhagen, Denmark, 1982, Develop Biol. Standard, vol. 55, pp. 103–111.

(List continued on next page.)

*Primary Examiner*—Robert A. Wax
*Assistant Examiner*—William H. Beisner
*Attorney, Agent, or Firm*—Banner, Birch, McKie & Beckett

[57] ABSTRACT

A fluidized bed reactor and reaction process, particularly well-suited for culturing cells, for example, for tissue culture and fermentation processes, are described which involve the treatment of at least a portion of the fluid exiting the fluidized bed reactor in a side loop in a manner to alter its temperature or composition, e.g., oxygenation, with recirculation of this treated fluid to the reactor as a portion of the fluid causing bed fluidization.

15 Claims, 8 Drawing Sheets

OTHER PUBLICATIONS

*Theoretical and Methodological Basis of Continuous Culture of Microorganisms*, p. 232 (Malek & Fencl eds. Academic Press 1966).

J. S. M. Botterill, *Fluid-Bed Heat Transfer*, pp. 263–271, (Academic Press 1975).

Leva, "Press Drop and Power Requirements in a Stirred Fluidized Bed," *A.I.Ch.E. Journal*, vol. 6, pp. 688–692 (1960).

Lewis et al., "Entrainment from Fluidized Beds," *Chemical Engineering Progress Symposium*, vol. 58, pp. 65–78.

Williams & Smith, "Heat Transfer in a Mechanically Stirred, Gas-Solid Fluidized System," *Chemical Engineering Progress Symposium Series*, vol. 66, pp. 70–74.

Brekken et al., "Fluidization of Flour in a Stirred, Aerated Bed: Part I: General Fluidization Characteristics," *Chemical Engineering Progress Symposium Series*, vol. 66, pp. 81–90 (1980).

Brekken et al., "Fluidization of Flour in a Stirred Aerated Bed: Part II: Solids Mixing and Circulation," *Chemical Engineering Progress Symposium Series*, vol. 66, pp. 277–284 (1970).

Reed & Fenske, "Effects of Agitation on Gas Fluidization of Solids," *Industrial and Engineering Chemistry*, vol. 47, pp. 275–282 (1955).

Kozulin & Kulyamin, "Mixing of Powdered Materials in a Fluidized Bed," *International Chemical Engineering*, vol. 5, pp. 157–161 (1965).

Nazemi et al., "Heat Transfer in Fluidized Beds of Flour and Starch," *A.I.Ch.E. Symposium Series*, vol. 67, pp. 106–113.

Couderc et al., "Echanges Thermiques en Fluidisation Gazeuse," *Chemical Engineering Science*, vol. 21, pp. 533–539 (1966).

Botterill & Williams, "The Mechanism of Heat Transfer to Gas-Fluidized Beds," *Trans. Instn. Chem. Engrs.*, vol. 41, pp. 217–230 (1963).

Feder & Tolbert (1983), *Scientific American*, 248:36–43.

Van Wezel et al., (1983) *In Vitro*, 19:259.

Feder et al., (1983) *In Vitro*, 12:260.

Karkare et al., (1985) *Biotechnology*, 3:247–251.

Karkare et al. (1983), "Immobilized Living Cell Systems for the Production of Fuels and Biochemicals", AIChE Diamond Jubilee Meeting, Oct. 31, 1983.

Dean and Venkatsubramian (1983), "Continuous Fermentation with Fluidized Slurries of Immobilized Microorganisms", American Chemical Society Annual Meeting, Aug. 30, 1983.

Karkare et al., (1984) "Continuous Production of Monoclonal Antibodies by Chemostatic and Immobilized Hybridoma Culture", American Chemical Society Annual Meeting, Aug. 27, 1984.

FIG. 6.
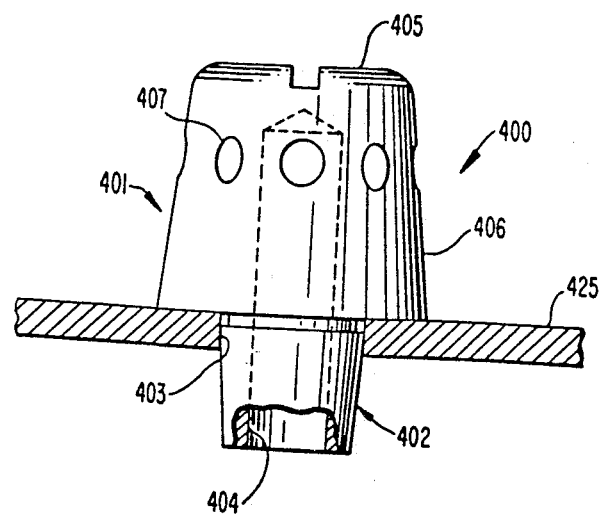
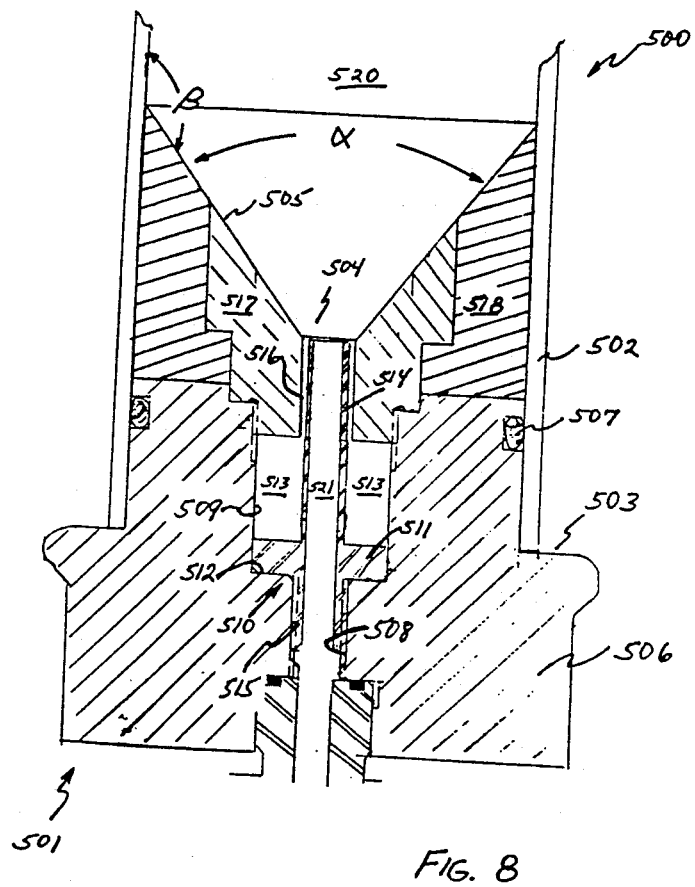
FIG. 8

FLUIDIZED CELL CULTIVATION PROCESS

This application is a continuation-in-part of earlier copending application Ser. No. 932,104 filed on Nov. 18, 1986, abandoned, in the names of Robert C. Dean, Jr., Peter V. Grela, Subhash B. Karkare and Peter W. Runstadler, Jr. which in turn was a continuation-in-part of earlier copending application Ser. No. 706,872 filed on Feb. 28, 1985, abandoned, in the names of Robert C. Dean, Jr., Peter V. Grela and Subhash B. Karkare which in turn was a continuation-in-part of earlier copending application Ser. No. 527,390 filed on Aug. 29, 1983, abandoned, in the name of Robert C. Dean, Jr.

BACKGROUND OF THE INVENTION

This invention relates to fluidized bed reactors for contacting fluids and solids, such as for carrying out chemical reactions, and particularly relates to processes for cultivating cells, e.g., tissue cultures and fermentations, using such reactors.

Fluidized bed reactors are known in which the fluid is delivered upwardly from the bottom of the reactor through a distribution plate or other resistance which stabilizes the fluidized bed. Stabilization is achieved by virtue of the positive resistance to flow offered by the distribution plate. The distribution plate tends to prevent gross distortion of the flow in the fluidized bed by offering lower resistance in regions having lower fluid velocity, and high resistance in regions of high velocity. Thus, the fluid flow tends to redistribute itself toward uniformity across the cross-section available for flow. A uniform fluid velocity profile is important to avoid channeling and other aberrant flow phenomenon which prevent good solids suspension and good fluid/solid contact. Typical examples of distribution plates known in the art are perforated metal plates, sintered materials, open-cell foams, and beds of pebbles. Fluid may be taken from the top of the fluidized bed and can be recirculated through a pump to the distribution resistance element or plate.

Fluidized bed reactors provide a convenient way for conducting chemical processes which require mass and energy transport between a solid and a liquid or gas. Such reactors potentially offer the advantages of high mass and energy transfer rates over a wide range of throughputs, and have been used in many applications.

In the fermentation-related art, various methods have been devised for immobilizing bioactive materials such as enzymes and microorganisms on or in bead-like supports, referred to herein as biocatalyst beads. Although often quite fragile, these beads generally are suitable for fluidization and thus offer the potential for adapting fluid bed technology to enzyme catalyzed processes and processes for cultivating cells. There are some problems, however.

Many processes for cultivating cells, such as fermentation processes, employ aerobic microorganisms and cells (in general "organisms"). These organisms demand a continuous supply of oxygen to remain viable. Normally, it is desirable to operate these processes at high solids concentrations, i.e., high cell densities, in order to maximize product yield. Unfortunately, in aerobic processes high cell densities exacerbate oxygen mass transfer demands, which, because of the fragile nature of the biocatalyst beads, cannot be met simply by increasing the level of agitation for increased oxygenation in the bioreactor. Also, in order to operate cell cultivation processes in a continuous manner at optimum conditions, means for controlling the reactor environment, including temperature adjusting means and means for supplying nutrients and other desired reactants to the cell culture and for removing products and by-products (both desirable and undesirable) from the cell culture, must be provided. Control of reactor conditions in this way must be accomplished without sacrificing the aseptic integrity of the system.

Another problem which can be especially acute in continuous cell culture processes utilizing very small biocatalyst beads containing immobilized microorganisms or enzymes is that conventionally designed perforated distribution plates may become plugged by solids or may permit back-flow of biocatalyst beads through the openings, for example, during periods of inactivity. In case of plugging, localized blocking is a typical result. Such blocking causes a change in the hydrodynamic conditions of the fluidized bed upsetting bed stabilization and necessitating that the reactor be shut down for the purpose of cleaning.

Of course, any solution to these problems must take into account the sensitive nature of the biocatalyst beads to physical impact forces and abrasion that might be encountered during operation as well as the sensitive nature of the immobilized bioactive material, especially mammalian cells. In a continuous process, a single charge of biocatalyst beads is expected to have a useful life on the order of six to eighteen months, so long as excessive attrition can be avoided.

SUMMARY OF THE INVENTION

It is therefore an object of one aspect of the present invention to provide a reaction method and a fluidized bed reactor therefor having a stabilized flow, which reactor is not prone to clogging during normal use.

It is an object of another aspect of the present invention to provide a reaction method and a fluidized bed reactor therefor, particularly suited for carrying out processes for cultivating cells.

It is a further object of the invention to provide a reaction method and a fluidized bed reactor therefor, in which minimal recirculation of solids occurs.

It is another object of the present invention to provide a method of continuous cell culture which can accommodate the oxygenation demands of an aerobic process without damaging the fragile biocatalyst beads or the cells immobilized in them.

Another object of this invention is to provide a fluidized bed reactor and method for continuously cultivating cells at high cell densities under optimum conditions while maintaining aseptic operation.

It is yet another object of the invention to provide a fluidized bed reactor which achieves the foregoing objects, and is simple in construction and operation, relatively inexpensive to manufacture and relatively easy to maintain in long-term, continuous aseptic use.

These and other objects of the invention are accomplished by providing a method of continuously contacting a liquid with a bed of particulate solids comprising: fluidizing the bed of solids with the liquid in a reaction zone; separating the solids from the fluidizing liquid at one end of the reaction zone; treating a portion of the separated liquid in a treatment zone, separate from the reaction zone, so as to alter the temperature or composition of the separated liquid; recirculating the treated liquid to the reaction zone as at least part of said liquid for fluidizing the bed of particulate solids; and recovering another portion of said separated liquid as product.

The method of the present invention has specific application in continuous aerobic cell culture processes wherein a bed of relatively fragile porous biocatalyst beads containing immobilized microorganisms or cells is fluidized with a liquid nutrient medium in a reaction zone. A liquid stream containing unconsumed nutrients and biochemical (metabolic) products is separated from the biocatalyst beads at one end of the reaction zone and a part of this stream is oxygenated in a separate treatment zone and is recirculated to the other end of the reaction zone for fluidizing the biocatalyst beads. A portion of the liquid stream containing unconsumed nutrients is removed to recover the biochemical product. Fresh nutrient medium is fed into the reaction zone at a rate equal to the removal rate of the portion of the liquid stream recovered as product; the feed rate yielding a feed dilution rate above the maximum specific growth rate of the microorganisms or cells.

In one embodiment, the fluidizing of the bed of solids comprises simultaneously pumping and stabilizing the flow of the liquid upwardly through a vertical reaction zone with a pump impeller located at the bottom of the reaction zone. The rotation of the impeller forces the liquid from below the impeller upwardly into the reaction zone to suspend the solids above the impeller, and the blades of the impeller are adapted to stabilize the velocity profile of the liquid above the bottom of the reaction zone without the need for any other stabilizing means above the impeller. In this embodiment, the diameter of the reaction zone may increase along the direction of upward flow of the liquid and this taper is such that when the liquid is in the fluidizing velocity range for the solids in the central portion of the reaction zone, the liquid in the bottom portion of the reaction zone is at a velocity above the fluidizing velocity range and liquid in the top portion of the reaction zone is at a velocity below the fluidizing velocity range.

One reactor for carrying out this particular process comprises a vertical reaction vessel and a bladed rotary pump impeller means at the bottom of the reaction vessel for simultaneously pumping the liquid nutrient medium and stabilizing the flow thereof upwardly through the reaction vessel to suspend the solids above the impeller means without the need for any other stabilizing means above the impeller means. Means are provided for supplying fresh liquid nutrient medium to the reactor, for withdrawing at least a portion of the liquid nutrient medium that has passed upwardly through the reaction vessel, and for recirculating liquid nutrient medium exiting the top of the reaction vessel to the bottom of the reaction vessel.

The preferred form of impeller is an open axial propeller having a relatively flat angle of blade setting which moves liquid through the fluidized bed at typical fluidization velocities of from about 0.01 to about 0.5 meters per second and which, through its dynamic action, stabilizes the bed in order to counter velocity distribution distortion that leads to nonuniform fluidized bed operation. A study of the velocity diagrams of the propeller shows that, where the axial (through flow) liquid velocity is low, the propeller adds more work because the effective angle of attack on the blade is increased. Conversely, where the axial velocity is high, the effective angle of attack decreases and so does the work input. Where the work input is high, there tends to be an increase of axial velocity countering the defect and vice-versa. The propeller has an "open" design, i.e., with large spaces through which the biocatalyst beads can pass. The probability of collision with the blades is therefore low and, because the blades move relatively slowly and with low power consumption, the incidence of damage to the beads and the bioreactive material, e.g., microorganisms, within them is low.

In another embodiment, the bed of solids is fluidized in a stable fashion by pumping the liquid into the bed of solids in a vertical reaction zone through a distribution plate having one or more nozzles which horizontally direct the flow of liquid substantially parallel to the surface of the plate comprising the bottom of the fluidized bed.

In still another embodiment, the bed of solids is fluidized in a stable fashion by pumping the liquid into the bed of solids in a vertical reaction zone through a distributor having a centrally positioned orifice and side walls which slope upwardly and outwardly to the inner wall of the reaction zone thus forming a conical pit at the base of the reaction zone.

As used herein, the term "biocatalyst bead" is used generically to catagorize supports containing immobilized bioactive materials such as enzymes, microorganisms and the cells of higher organisms, particularly microorganisms and cells requiring a constant supply of oxygen for proper development, including without limitation bacteria, fungi, plant cells and mammalian cells (e.g., hybridomas). Such beads can be used in connection with a wide variety of processes and the present invention is directed to a fluidized bed method and apparatus for carrying out such processes.

Normally, suitable beads will have a porous structure and may be fibrous or sponge-like in appearance. Particular pore sizes and structure needed for specific microorganisms and cells will be apparent to those skilled in the art. For example, for hybridomas, which are roughly spherical and are about 10–15 microns in diameters, an appropriate pore size for the beads is about 20–40 microns. This porous structure, which preferably has interconnected channels, permits microorganisms and the cells of higher organisms to become mechanically entrapped in the beads and then to colonize the beads. Cell entrappment and colonization of the beads (cell immobilization) can occur merely by inoculating the nutrient suspending liquid and then initiating operation of the fluid bed reactor. This porous structure also permits excess cells from an expanding immobilized colony and any products produced by immobilized cells to escape from the beads into the fluidizing liquid. Suitable beads can be prepared using a wide variety of materials including, inter alia, natural polymers such as polysaccharides and fibrous proteins, synthetic polymers, such as polyamides (nylon), polyesters and polyurethanes, and minerals including ceramics and metals.

Also as used herein, phrases such as "process for cultivating cells," "cell culture process" and the like are intended to embrace a wide variety of biochemical processes involving bioactive materials. These phrases embrace processes in which microorganisms or the cells of higher organisms are cultured, using an appropriate nutrient medium, to enhance the production of desired metabolic products. For instance, metabolite production by continuous culture of mammalian cells is specifically included within the intended meaning of these phrases. Among the mammalian cells which find utility in the process of the present invention include hybridoma cells, Chinese Hamster Ovary Cells (CHO), Transformed Rat Kidney Cells, Mouse Mammary Cells, African Green Monkey Kidney Cells, Baby Hamster Kidney Cells and Human Embryonic Kidney Cells. These cells are commonly genetically engineered to provide for expression of protein products such as antibodies, lymphokines, growth hormones, blood proteins and anticancer products. As an example, see British Patent No. 2,119,804B which describes techniques for constructing and culturing a CHO cell line genetically engineered to produce tPA.

BRIEF DESCRIPTION OF THE DRAWINGS

The novel features of the invention are set out with particularity in the appended claims, but the invention will be understood more fully and clearly from the following detailed description of the invention as set forth in the accompanying drawings, in which:

FIG. 6 is a schematic illustration of a nozzle which when used on the distribution plate of a vertical reactor substantially horizontally directs the flow of liquid parallel to the distribution plate at the bottom of a fluidized bed reactor.

FIG. 8 is a schematic sectional view of a distribution assembly for a fluidized bed reactor having a single conical pit.

DETAILED DESCRIPTION

Although this detailed description is in the context of a fluidized bed reactor used in continuous cell culture processes, including fermentation processes, it is to be understood that the apparatus itself is suitable for use in many different types of processes involving fluid and solid contact. While described primarily in the context of liquid/solid contacting it will be appreciated that aspects of the method and the apparatus are also suited for any fluid, i.e., liquid, gases or mixtures thereof. In such fluidized bed processes it is known that a wide variety of forces can be used to generate and stabilize the counterflow of fluid and solids needed to operate a fluidized bed reactor. While the present invention will be described using an embodiment in which a pressurized liquid and the force of gravity play the primary roles in the operation of the fluidized bed, the present invention is not intended to be so limited. Those skilled in the art will readily appreciate other available embodiments employing other physical phenomena.

Figure 1:
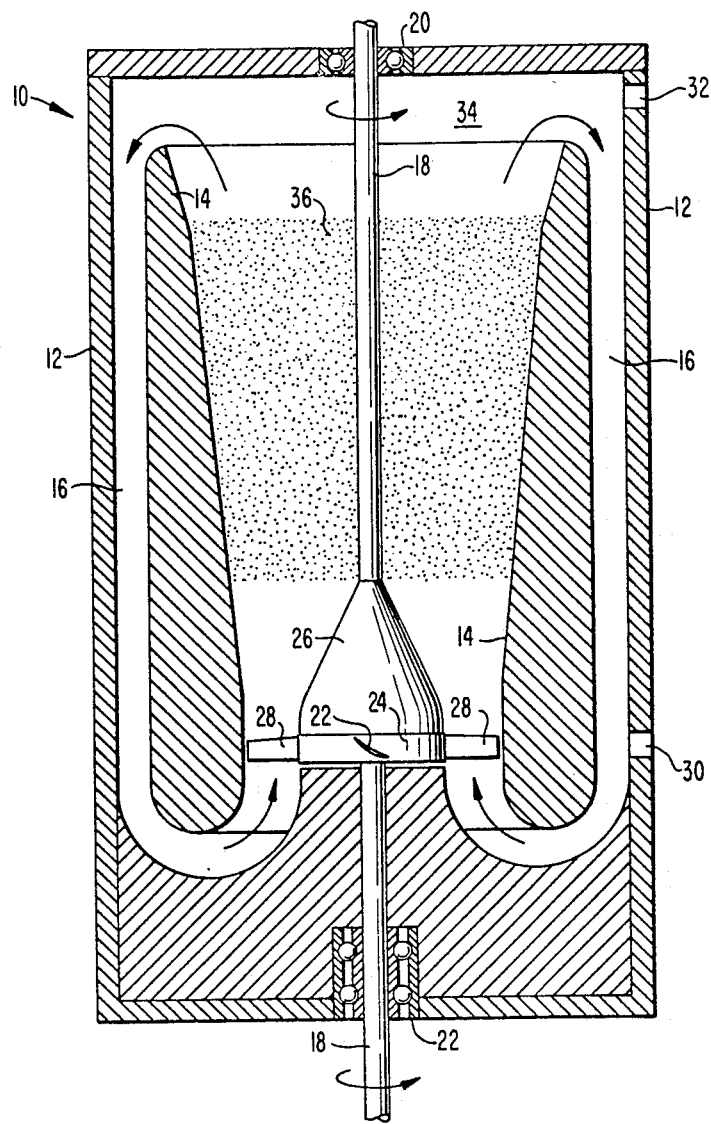
FIG. 1 is a schematic vertical sectional view of a fluidized bed reactor in accordance with one embodiment of the invention.

Referring to FIG. 1, a fluidized bed reactor 10 in accordance with one embodiment of the invention comprises a containment vessel 12 having within a stationary, tapered reaction vessel 14. An annular recirculation channel 16 provides fluid communication between the top and bottom portions of reaction vessel 14. A rotatable shaft 18 is journalled in bearings 20,22 in the upper and lower portions of containment vessel 12. A propeller 24 is fixed to and rotated by shaft 18, along with propeller tail cone 26. Tail cone 26 and the surrounding portion of reaction vessel 14 function as a diffuser to spread the liquid flow evenly across the entire cross-section of the reaction vessel. Propeller 24 has blades 28 and is of a substantially open design as described below. An inlet 30 is provided for supplying fresh liquid nutrient medium to the reactor. Outlet 32 permits the withdrawal of at least a portion of the liquid nutrient medium or fermentation liquor that has passed upwardly through the reaction vessel 14. During operation, reaction vessel 14 and the recirculation channel 16 are substantially filled with liquid nutrient medium, while a fluidized bed of biocatalyst beads, for example polysaccharide gel beads containing entrapped microorganisms, is maintained suspended in the central portion of reaction vessel 14 above the propeller.

As seen in FIG. 1, the inner diameter of the reaction vessel 14 increases along the direction of upward flow of the liquid nutrient medium. The taper of reaction vessel 14 is such that when the liquid nutrient medium is in the fluidizing velocity range for the beads 36 in the central portion of the reaction vessel, the liquid nutrient medium in the bottom portion of the reaction vessel, just above propeller 24, is at a velocity above the fluidizing velocity range, and the liquid nutrient medium in the top portion of the reaction vessel is at a velocity below the fluidizing velocity range. The fluidizing velocity range is, of course, that range of upward fluid velocity of liquid nutrient medium 34 which overcomes the gravitational force on the biocatalyst beads 36 and maintains them in suspension with substantially little or no net movement of the beads either upward or downward. Typical fluidization velocities may be on the order of about 0.01 to about 0.5 meters per second for biocatalyst beads having a size of about 0.1 mm up to about 0.5 mm or more.

While this embodiment and others are described in connection with a fluidized bed arrangement in which an upwardly flowing stream of pressurized liquid suspends a bed of solids against the downward pull of gravity, as will be apparent to those skilled in this art, the invention also is applicable to arrangements employing low specific gravity solids, such as biocatalyst beads having a buoyancy which exceeds the gravitational force, where the fluidizing fluid flow is directed downwardly through the bed of buoyant solids.

In a manner known in the art, the tapered bed can be replaced with other forms so long as means are provided to separate the solid particles from the fluidizing medium, such as for example a straight wall reactor with a stepped expansion zone at its upper end or utilizing various known separation devices employing centrifugal, magnetic, electrostatic (electrical) or gravitational forces. Moreover, in the preferred method for operating the present invention in connection with cell culture processes at high concentrations (densities) of biocatalyst beads, i.e., at a void volume of less than about 75% of the reaction zone volume as will be described in more detail hereafter, the separation of solids particles from the fluidizing medium is very distinct and only a minimal amount of freeboard, without necessity for precautionary designs such as tapered or stepped expansion zones, is needed to ensure satisfactory removal of the bead solids from the fluidizing liquid.

Propeller 24 is designed to effect suspension of the particulate bed and stabilization of the fluid velocity above the propeller without any other stabilization means and to avoid damage to any recirculating solids. To these ends, the propeller should have an open design having large spaces through which biocatalyst beads 36 can pass undamaged. More specifically the preferred propeller design has a solidity value of less than 1.0. Solidity is the ratio of the propeller blade chord to the blade spacing. Moreover, the blade angle should be set very flat, i.e., typically not more than about 15° off a tangent to the axis of rotation. The propeller blade profile is designed to move high volumes of fluid with a small rise in pressure, as in the case of cooling tower fans and the like. Suitable for this purpose are conventional airfoil types such as those in the NASA 6500 series. The impeller of the present invention should also be adapted to run at a slow speed with low power consumption. Quantitatively, the propeller blade tip speed preferrably varies in the range of from about 12 to 24 times the fluidizing velocity, which in turn ranges from about 0.01 to about 0.5 meters per second depending on the bead size, bead material specific gravity and fluidizing medium viscosity. For the biocatalyst system described herein, the tip speed preferrably ranges from about 1 to about .10 meters per second. The propeller power requirements of this low speed propeller are very low e.g., less than about 0.25 kilowatt for a 1000 liter reactor, excluding losses for seals and bearings.

Figure 2:
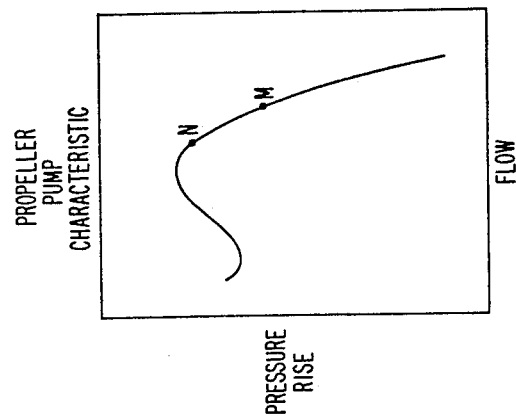
FIG. 2 is a propeller characteristic plot of fluid pressure rise as a function of fluid flow.

FIG. 2 illustrates a typical propeller characteristic representing fluid pressure rise as a function of flow across the propeller. The characteristic graphically illustrates the stabilization effect that the propeller has on the fluidized bed. When the local flow up into the fluidized bed tends to decrease (represented by a movement of the operating point from desired point M to a lower flow point N), then the propeller pump generates a higher pressure as shown. This higher pressure tends to increase the fluid flow and move operation from point N back to the desired point M. Thus, the fluidized bed is stabilized, that is, the velocity profile distortions tend to be eliminated by the propeller's action. The "steeper" the propeller's characteristic (i.e. the flatter the blade setting), the stronger the stabilizing action.

Figure 3:
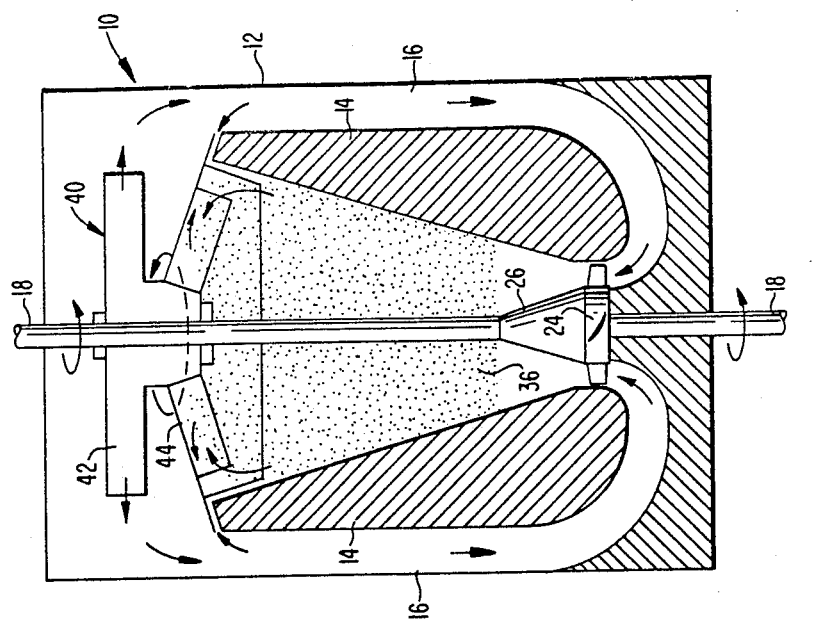
FIG. 3 is a schematic view of a fluidized bed reactor in accordance with a another embodiment of the invention.

Even though the reactor of FIG. 1 tends to maintain a stable fluidized bed, a small amount of biocatalyst beads nevertheless may unavoidably escape over the top of reaction vessel 14 and be entrained in the recirculation flow through channels 16 and propeller 24. While the design of propeller 24 minimizes attrition of the biocatalyst beads 36, it may be desirable to further minimize the recirculation of beads 36 by providing, as illustrated in FIG. 3, a rotary centrifugal separator 40 at the upper end of reaction vessel 14. Separator 40 includes a vaneless rotating diffuser 42 and a bead-separating bladed centrifuge 44, both of which are rotatably driven by shaft 18 which extends upwardly from impeller 24 through reaction vessel 14. Bead-separating centrifuge 44 slings any beads 36 which rise within it along with upwardly flowing liquid nutrient medium 34 outwardly and back downwardly into reaction vessel 14. Vaneless diffuser 42 recovers the kinetic energy of the flow and converts it to a pressure rise.

As noted, if necessary or desired, other arrangements for separating beads from the fluidizing medium also could be employed including those operating by means of magnetic or electrical forces. Also, a cyclonic separator, e.g., Hydroclone, could readily replace the disclosed rotary centrifugal separator. Various arrangements are readily apparent to those skilled in the art.

Figure 4:
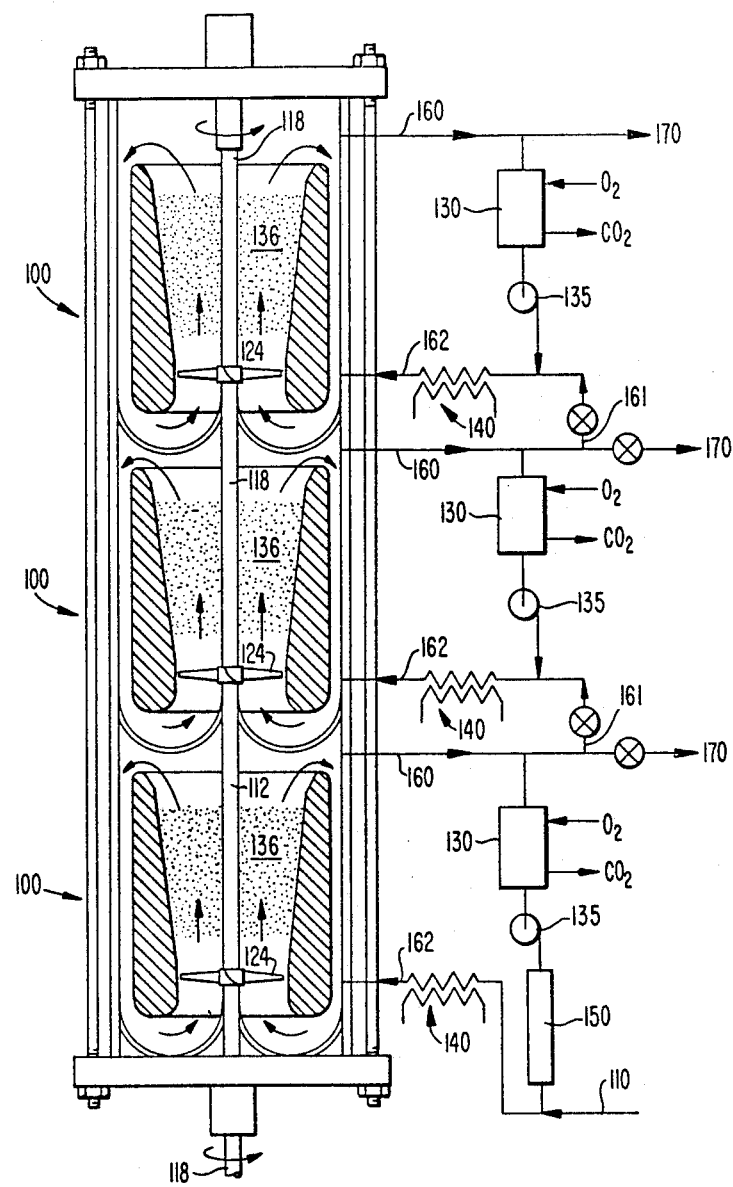
FIG. 4 is a schematic view of a multi-stage fluidized bed reactor in accordance with the invention.

An especially efficient arrangement for conducting cell culture processes, including fermentation processes, and particularly aerobic processes, is illustrated in FIG. 4. FIG. 4 shows a multi-cell fluidized bed reactor made up of a serial arrangement of individual reactors 100 such as that illustrated in FIG. 1. All of the propellers 124 of the several individual reactors 100 are driven by a common shaft 118. Treatment of the recirculating culture liquid to maintain optimum conditions in reactors 100, such as aeration and/or, $CO_2$ extraction e.g., in a membrane gas exchanger 130; heat exchange to heat or cool the culture liquid in exchanger 140; filtration at 150; or other treatment such as pH control, sterilization (e.g., by filtration, UV irradiation or ozonation) and altering the composition of the recirculating fluid such as by adding nutrients or other bioactive materials to the recirculating fluid or by removing desirable and/or undesirable metabolic products therefrom using any of a wide variety of techniques, for example, is accomplished by withdrawing side loops 160 from each reactor 100 and effecting the necessary treatment in a separate treatment zone without injuring the fragile biocatalyst beads 136 or disturbing conditions within the reactor 100 itself. Additionally, a portion of the withdrawn side loops 160 from the bottom and middle reactors 100 is used as a feed stream 161 for the middle and top reactors 100, respectively, which is combined with their respective recirculating fluid. Such treatments result in a change in the temperature and/or composition of the culture liquid. The treated liquid then is recirculated to the associated reaction zone via input lines 162 with the aid of pumps 135 as at least part of the fluid for fluidizing the bed of solids 36. For the bottom reactor 100, the recirculating fluid is combined with fresh liquid nutrients medium supply 110. Generally, the recirculated liquid comprises the major part of the fluidizing flow.

Product streams 170 can be taken off at any desirable stage in the process. The reactor may be operated hyperbarically to ten or more atmospheres in order to proportionally enhance the oxygen carrying capacity of the recirculating liquor. By using a side loop to effect treatment of the culture liquid, and thus treatment of the immobilized bioactive material on or in the biocatalyst beads, it is possible to maintain optimum conditions without jeopardizing aseptic operation or damaging the fragile biocatalyst beads or immobilized bioactive material. This arrangement also permits separate control of the feed rate of fresh nutrient medium and the flow rate of the recirculating culture liquid.

Figure 5:
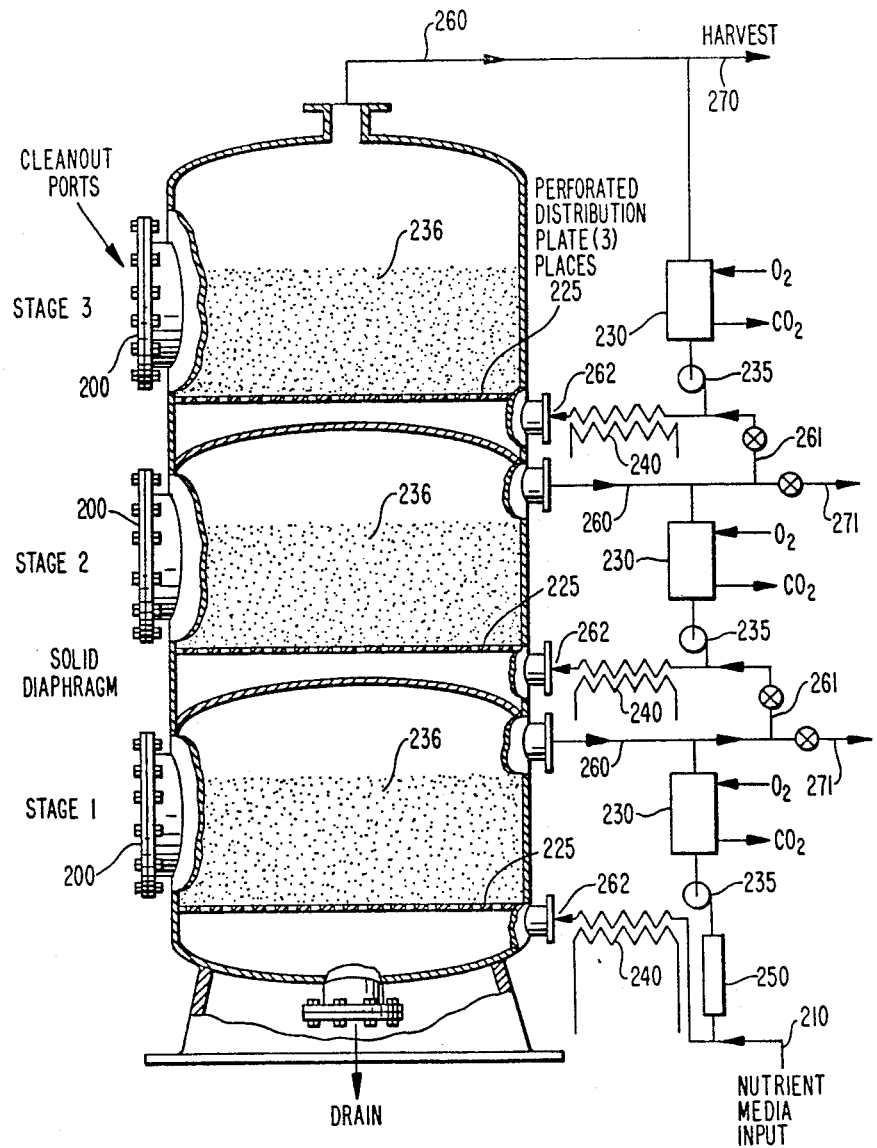
FIG. 5 is a schematic view of a multistaged fluidized bed reactor having a conventional perforated distribution plate in accordance with another embodiment of this invention.

FIG. 5 shows an alternative arrangement to FIG. 4. FIG. 5 employs a serial or parallel arrangement of individual reactors for conducting a cell culture process in accordance with this invention. While both aerobic and anaerobic processes are contemplated, this embodiment is directed to the cultivation of cells and microorganisms which require the continuous supply of oxygen for proper development. In FIG. 5, elements corresponding to elements in the FIG. 4 arrangement are identified by reference numerals having the same last two digits. FIG. 5 differs from FIG. 4 in that instead of employing a propeller, the bed of solids 236 in each reactor 200 is fluidized by pumping the fluid through a distribution plate 225 which stabilizes the fluidized bed. In the broad practice of the method of the present invention, the fluidized bed reactors may employ any of a wide variety of available distribution designs including, inter alia, a perforated plate or sieve tray, a slotted tray, a pebble bed, e.g., glass beads, a porous ceramic, an open cell foam and a sintered metal.

While FIG. 5 illustrates a conventional perforated distribution plate, in order to avoid plugging and backflow of solids through the distribution means, for example, during inoperative periods, particularly in the case where fragile biocatalyst beads are being fluidized by and reacted with a liquid nutrient medium, the normal perforations in the conventional distribution plate can be replaced with one or more horizontal flow-directing nozzles in a suitable array. A suitable nozzle design is illustrated in FIG. 6. As shown, the nozzle 400 consists of an enlarged head member 401 and a stem 402. The head member has a top surface 405 and a generally vertical side wall 406. As shown, the nozzle can be provided with any cross-section although a cylindrical shape is convenient. The stem 402 is sized for a friction fit with a perforation 403 in the distribution plate 425. The stem has a centrally located bore 404 which extends into head member 401 (indicated by dotted outline). The side wall of the head member is provided with substantially horizontal ports 407 which communicate with bore 404. Preferably, the ports are equally spaced around the circumference of the nozzle. For example, a normal ¾ inch diameter nozzle may have twelve, approximately ⅛ inch diameter, ports equally spaced about its circumference. In operation, liquid (and biocatalyst beads when occasionally recirculated) passes through the distribution plate by flowing through bore 404 and then radially outwardly (horizontally) through ports 407 into the fluidized bed reactor. In addition to reducing plugging and back-flow of solids, such nozzle designs also reduce the incidence of stagnant regions in lower corners of the reactors.

The number and arrangement of such nozzels in any application is, among other things, a function of the size of the reactor and the characteristics of the biocatalyst beads. For example, in a small reactor (diameter of about 2-4 inches) a single centrally located nozzle generally would be sufficient; while in a larger reactor (e.g., a diameter of about 8 inches) about 16 nozzles positioned in a symmetric pattern on the distribution plate should be employed. If advantageous, a bed of pebbles, e.g., glass beads, of an appropriate diameter, also can be supported by the distribution plate fitted with said nozzles to further stabilize performance. The number and arrangement of such nozzles for any particular application is within the skill of the art. Generally, the nozzles are designed so that fluidization velocities in the range of about 0.001 to 0.01 m/sec are achieved at a pressure drop through the nozzle on the order of about 0.1 to about 1.0 psi using the heads of the desired characteristics.

Figure 9:
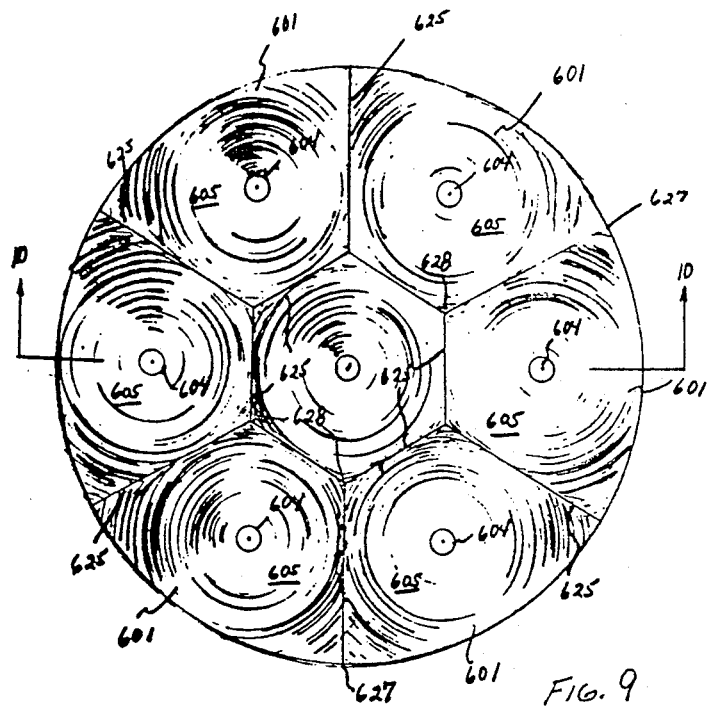
FIG. 9 is a schematic overhead view of a distribution assembly for a fluidized bed reactor having multiple conical pits of the type illustrated in FIG. 8.
Figure 10:
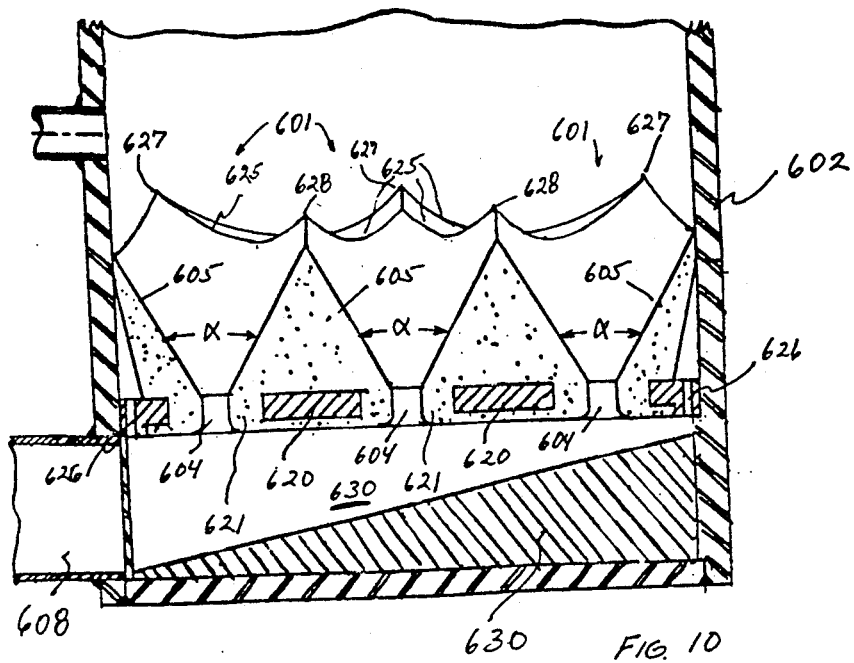
FIG. 10 is a schematic view, partly in section, of the multiple conical pit distribution assembly of FIG. 9 taken along line 10—10 of FIG. 9.

Alternative preferred distributor arrangements for delivering fluidizing liquid to the bottom of a fluidized bed for fluidizing biocatalyst beads therein are illustrated in FIGS. 8, 9 and 10. Referring first to FIG. 8, a suitable distributor design for a small fluidized bed reactor, e.g., having 1 liter volume, a diameter of about 50 mm and an expanded bed depth of about 300 mm, is illustrated. As shown, the distributor assembly 501 is located at the base of a cylindrical vertical reactor 500. The distributor comprises a centrally positioned orifice 504 and an upwardly and outwardly sloped side wall 505. The side wall 505 forms an obtuse angle B with the cylindrical side wall 502 of reactor 500. In this embodiment, orifice 504 may have an inner diameter of about 6.75 mm. The depth (length) of orifice 504 is a matter of choice and shorter or longer designs than that illustrated in FIG. 8 are possible. In fact, in many cases shorter lengths are desirable to minimize the possibility of plugging. The sloped side wall 505 of distributor 501 forms a conical pit or funnel at the base of the fluid bed reactor having an included or divergent angle (alpha) within the range of about 50° to 70°, preferably about 60°. In this embodiment, the sloped side wall is formed by interfitting pieces 517 and 518; but obviously could be formed from a single element.

In the specific embodiment illustrated in FIG. 8, the cylindrical side wall 502 of reactor 500 is supported on a ledge 503 of reactor base 506. The reactor side wall 502 is sealed with respect to base 506 by gasket 507. Reactor base 506 is provided with an inlet bore 508 and an enlarged bore section 509 located upstream thereof forming inner ledge 512 at their intersection. Jet nozzle element 510 has a flange 511, two outwardly extending tube portions: tubular nozzle portion 514 and tubular inlet portion 515, and an axial bore 521. Since the beads may have a diameter as large as about 1000 microns (1 millimeter), the minimum diameter for bore 521 of nozzle element 510 is about 1.5 mm in order to pass beads accidently recirculated. In the specific embodiment shown, the bore 521 of jet nozzle element 510 has an inner diameter of about 2.4 mm. Jet nozzle element 510 screws into inlet bore 508 until flange 511 rests on inner ledge 512 of base 506, thus forming an annular region 513. As described in more detail below, annular region 513 plays an important role in prolonging the life of biocatalyst beads weighted with a metal or mineral.

The outlet end of nozzle portion 514 of jet nozzle element 510 terminates in the vicinity of the outlet or downstream end of orifice 504. Fluidizing liquid is injected, without fixed obstruction during operation, vertically into the fluidized bed through jet nozzle element 510. With proper design and by appropriately establishing the recycle flow rate, a recirculating zone or eddy of fluidizing liquid having a depth of approximately two bed diameters can be established in region 520 above distributor 501. Biocatalyst beads circulate down along the reactor side wall 502 and then down the sloped (conical) wall 505 of distributor 501 where, in the vicinity of the orifice 504 and nozzle 514, the beads are entrained in the liquid jet flowing through nozzle 514. Above the recirculation region, the fluidizing liquid flow tends to be directed upwardly in a radially uniform manner yielding a well-stirred and homogeneous fluid bed. This design thus eliminates stagnant areas which pose severe fouling problems for fluidized beds used for culturing microorganisms and cells.

The outer diameter of the tubular nozzle portion 514 of jet nozzle element 510 is sized so that a small annular opening or gap 516 is formed between the inner wall of orifice 504 and the outer surface of the nozzle portion 514 of jet nozzle element 510. In the specific embodiment shown the nozzle portion 515 of the jet nozzle element 510 has an outer diameter of about 6.35 mm.

Thus, annular gap having a width of about 0.4 mm is formed between the opposing surfaces. This annular gap serves as a passage between the main reactor volume 520 of the fluidized bed and the annular region 513.

Annular region 513 constitutes a sump or trap for collecting any mineral or metal weighting pieces which have become dislodged from the biocatalyst beads. Generally such weighting pieces will be smaller than about 100 microns (0.1 mm), and thus readily pass from the fluid bed through the annular gap 516 into annular region 513. However, the gap is small enough to prevent beads from passing into the annular region when fluidization ceases. Without this trap, free mineral or metal weighting pieces would collect in the vicinity of the fluid jet emitted from nozzle 514. These pieces would be agitated by the liquid jet issuing from nozzle 514 and the motion of the weighting pieces would have the same effect as a "ball mill" on the biocatalyst beads in the vicinity of the nozzle, leading to high bead attrition and cell damage in this area. The design illustrated in FIG. 8 has proven to be suitable for long term fluidization of biocatalyst beads having a diameter of approximately 500 microns and a specific gravity of about 1.2. Suitable distributor dimensions for biocatalyst beads of different sizes and/or different specific gravities can be identified by those skilled in the art using routine experimentation.

In cases where bead attrition caused by free weighting pieces is not a problem, use of a jet nozzle having a smaller outer diameter than the diameter of orifice 504 of distributor 501 and the provision of annular space 513 in the assembly can be eliminated. The distributor thus would comprise simply a conical pit or funnel with a centrally positioned orifice, the orifice functioning as the jet nozzle (see FIG. 10).

The high fluidization velocity in the region of orifice 504, in addition to generating the recirculation flow which as described above, eliminates stagnant areas at the bottom of the fluid bed reactor, also permits biocatalyst beads, some of which occasionally escape from the bed, to be returned to the fluid bed without plugging via the recirculating fluidizing liquid introduced through inlet bore 508.

While the distributor of FIG. 8 has been described specifically in connection with a 1 liter reactor, it can be scaled-up for larger diameter reactors simply by enlarging the orifice and jet nozzle element dimensions. The area ratio between the reactor cross-sectional area contiguous to the distributor 501 and the jet nozzle for the fluid reactor is above about 30 and for a six inch diameter reactor preferably is fixed within the range of about 40 to 100, preferably about 60. Additionally, while the distributor arrangement illustrated in FIG. 8 is fabricated from four separate pieces, those skilled in the art will recognize that a fewer number of pieces could be used to form a similar distributor assembly.

In an alternative embodiment, illustrated in FIGS. 9 and 10, scale-up of the conical pit distributor design of FIG. 8 is accomplished simply by providing a symmetrical grid of multiple conical pits or funnels 601 each having substantially the same jet orifice diameter and divergent angles. Since fluidized beds scale at constant bed depth, i.e., fluidized beds scale horizontally, and since it generally is desirable that the fluid dynamic characteristics of a fluidized bed distributor not change as a consequence of scale-up, use of multiple conical pits as illustrated in FIGS. 9 and 10 provides a advantageous way for providing a distributor design for larger reactors. By maintaining substantially the same dimensions, the fluid dynamic characteristics of each conical pit or funnel remains substantially constant. The specific number of pits needed for a particular size of reactor depends on a variety of factors and suitable designs will be readily apparent to those skilled in the art.

As shown in FIGS. 9 and 10, the distribution assembly has seven distributors 601 each containing an orifice 604 centrally located in the seven symmetrically positioned conical pits or funnels each having sloped side walls 605. Ridges 625 are formed at the intersection of the upper ends of the side walls of the various conical pits or funnels and along the upper circumferential edge of the distributor. FIG. 10 illustrates a cross-sectional view of the FIG. 9 design taken along line 10—10. As illustrated in FIG. 10, the ridges at the upper end of the distributors 601 have a scalloped effect. The highest points 627 of the scallop are located at the outer circumference of the distributor, while intermediate points 628 are located at the three-way intersection of the ridges spaced around the center conical pit.

The FIGS. 9 and 10 distributor design can be prepared in a variety of ways. For example, the distributor arrangement illustrated in FIGS. 9 and 10 can be prepared by casting a suitable plastic or elastic material such as polycarbonates or silicone rubber around a reinforcement plate 620 provided with an array of circular openings 621 having their center lines oriented in line with the center line of the desired positions for orifices 604. The outer edge of the reinforced plate 620 also is provided with small openings 626 which facilitate steam sterilization of the assembly. The side walls 605 of the conical pits and the orifices 604 then are machined using appropriate tooling that will be obvious to those skilled in the art.

In contrast to the FIG. 8 design, in the FIG. 9 and 10 assembly orifices 604 also function as the fluidizing liquid injection means or jet nozzles. In order to provide a uniform flow of fluidizing fluid through the numerous orifices or nozzles 604 of the conical pits 601, the upstream inlet region 630 for the distribution assembly may be suitably contoured so as to proportion the flow of the fluidizing liquid equally through the various orifices. Suitable designs for proportioning the flow will be apparent to those skilled in the art. The fluidizing liquid flows into region 630 through conduit 608 and then is injected into the fluid bed at a high fluidation velocity through the orifices 604. In an alternate design, to prevent biocatalyst beads from falling through the nozzle when the bed is de-activated, leaf, flapper or "duck bill" valves, e.g., made of a suitable elastomer like silicone rubber, could be employed in the nozzle as could other valving means common to the fluidized bed art.

Another alternate distributor design (not shown) utilizing the concept of multiple pits provides numerous orifices in the center of annular ring segments of approximately constant width. The segments are formed by subdividing annular rings with radial dams or dividers. The radial dams are positioned so that each annular segment has an approximately equal circumferential length. The side walls of each annular segment then are sloped downwardly and inwardly to the centrally positioned orifice. Thus, this design provides repeating annular shaped conical pits or funnels.

Referring back to FIG. 5, the reactors 200 are designed and operated so that the biocatalyst beads readily separate from the upwardly flowing fluidization liquid in the upper region of each reactor. Any of the arrangements identified above in connection with FIGS. 1, 3 and 4 for effecting this separation could be employed. With a thick slurry of beads (e.g., 25%–60% solids), however, which is preferred, it is sufficient to rely on the force of gravity simply by providing a small disengagement zone (free-board) above the expected (design) level of the expanded bed. When operating at such high concentrations of the biocatalyst beads, the separation of solid particles from the fluidizing liquid is very distinct, eliminating the need for any precautionary designs such as a tapered disengagement zone or centrifugal separators.

Fresh nutrient medium is introduced into stage 1 of the reactor assembly of FIG. 5 through line 210 and a portion of the unconsumed nutrient medium, discharged in lines 260 from stages 1 and 2 respectively, is passed to the succeeding stages 2 and 3 through lines 261 and 262 as feeds for these stages. Product is removed from the reactor arrangement primarily through line 270 of stage 3. Under steady state operation, since the total reactor volume is fixed, the rate of introduction of fresh nutrient medium in line 210 is equal to the rate of product removal through line 270. In the FIG. 5 embodiment, the quotient of the volumetric flow rate of fresh nutrient medium and the total system volume (i.e. reactor volume plus volume of recirculation loop) represents the feed dilution rate (unit of time$^{-1}$) or fresh nutrient dilution rate and represents the inverse of the nutrient residence time in the reactor.

As shown in Examples 2 and 3, in carrying out the method of the present method, feed dilution rates above that corresponding to the specific cell growth rate of the microorganisms being cultured can be and are preferably used. This high rate of dilution unavoidably leads to a reduced number of free cells suspended in the fluidizing nutrient liquid between the biocatalyst beads and a high rate of elution of free (i.e. non-immobilized) cells from the reactor. Certain advantages inherent in this way of operation relating to initial bead colonization and stability of the microorganisms or cells cultured will be discussed in more detail hereafter.

Lines 271 can be used either for adding additional material to stages 2 or 3 or for withdrawing a portion of the unconsumed nutrient medium from stages 1 or 2, for example, for analysis or interim product removal.

In this embodiment, each bed of biocatalyst beads 236 contains an immobilized bioactive material that requires oxygen to remain active. Exemplary bioactive material includes aerobic microorganisms and cells such as aerobic bacteria, fungi and mammalian cells. The beads may consist of a polysaccharide gel such as carrageenan or agarose gels entrapping the microorganisms and cells. Other bead supports include natural and synthetic polymers, ceramics and metals. The beads generally are porous and may be fibrous or sponge-like in appearance. Preferably, the beads comprise a highly crosslinked fibrous polymer such as collagen in which the microorganisms are entrapped.

The bead porosity facilitates colonization of the beads and expulsion from the beads of extra-cellular products and excess cells from an expanding colony. Colonization can be accomplished simply by inoculating the fluidizing liquid with the microorganisms or cells and then initiating operation of the reactor. For example to culture a hybridoma, the fluid bed can be inoculated with a seed culture to provide 2 to $5 \times 10^5$ hybridoma cells per milliliter of reactor volume. A suitable inoculation culture can be prepared, for example, using known batch or chemostat culture techniques. Thereafter, cells are taken up slowly by the beads and the free cell density in the fluidizing liquid declines. After a period of incubation, e.g. 7–10 days in the case of hybridomas, the cell colony in the beads achieves a density of about $0.5-2 \times 10^8$ cells per milliliter.

The high feed dilution rates used in the methods of Examples 2 and 3 assist the rapid colonization of the beads by the microorganisms or cells. Although not wishing to be limited to any particular theory, applicants believe that by minimizing the free cell concentration in the fluidizing liquid, the high feed dilution rates used in Examples 2 and 3 increase the quantity of nutrient available to cells immobilized in the beads. Under this enhanced nutrient environment, immobilized cells experience a rapid growth leading to rapid population of the beads. Rapid population of the beads, in turn, leads to a rapid achievement of steady state conditions and high reactor productivity in a short time. At lower feed dilutions rates, the fluidizing liquid would have a higher free-cell concentration. Depletion of nutrients by such an increased population of suspended cells would tend to deprive immobilized cells of needed nutrients, thus retarding their growth.

Generally, to improve fluidization behavior the beads will be treated to alter their specific gravity. The beads may be weighted with an inert material, such as silica, stainless steel or titanium to suitably increase their density above the density of the fluidizing medium. Alternatively, the beads may include entrapped gas to lower their density. A particularly preferred fibrous polymer bead can be manufactured from collagen, e.g., using known procedures. A particularly preferred procedure for manufacturing collagen beads is described in the copending U.S. application of Robert C. Dean, Jr., Frederick H. Silver, Richard A. Berg; Phillip G. Phillips and Peter W. Runstadler, Jr. filed on Apr. 4, 1985, and assigned Ser. No. 719,881, the disclosure of which is incorporated herein by reference.

The bed of biocatalyst beads in each reactor stage is simultaneously fluidized and oxygenated by recirculating a major portion of the unconsumed nutrient medium discharged from each reactor stage in lines 260 through a side loop. The portion of the unconsumed nutrient medium discharged in line 260 and circulated for fluidizing the bed of biocatalyst beads is first passed through the oxygenators 230 where the dissolved oxygen content of the liquid is increased by contacting the liquid with an oxygen-containing gas. While a wide variety of devices can be selected for oxygenating the recirculating fluid, including porous fine-bubble diffusers, mechanical aerators, or membrane oxygenators, membrane devices generally will be preferred for aerobic cell culture applications. Fine bubble diffusers and mechanical aerators tend to be plagued by foaming problems. Moreover, certain mediums and products, such as those encountered when culturing mammalian cells, tend to be sensitive to the presence of a liquid-gas interface thereby obviating the selection of any device as the oxygenator which depends upon the generation of a large surface area of small bubbles for gas transfer. Membrane oxygenators transfer the oxygen directly into the liquid on a molecular level without any gas-liquid interface. Membrane oxygenators suitable for fermentation applications include commercially available blood oxygenators such as available from Cobe, Denver, Colo.; American Bentley Corp., Irvine, Calif., and SciMed Co., Minneapolis, Minn. Microporous filters such as the Gelman Acroflux cartridge Gelman Sciences, Inc., Ann Arbor, Mich., and the Millipore Millidisk, Millipore Co., Milford, Mass., may also be used in appropriate circumstances.

A particularly preferred oxygenator, based on both design simplicity and performance characteristics, is a shell and tube oxygenator employing tube material having a suitable oxygen permeability. Any of the well-known shell and tube-type designs used for example in the heat transfer art can be employed. See, for example, Perry, R. H. and Chilton, C. H., *Chemical Engineers' Handbook*. A particularly useful design simply comprises a single helical strand of suitable tubing in a pressure vessel. Silicone tubing having an oxygen permeability on the order of about $1.3-1.4 \times 10^{-6}$ mmols $O_2$-mm per $cm^2$-cm Hg per minute has proven to be particularly effective as tube material. Of course, other materials having different oxygen permeation characteristics can be employed. The selection of suitable materials and gas exchanger designs is within the skill of the art. With this arrangement, oxygen mass transfer rates of up to 40 mg-mols oxygen per liter of reacter volume per hour have been attained at a recycle dilution rate of 150 $hour^{-1}$.

By properly selecting the tube material, it also is possible to effectively remove carbon dioxide from the recirculating liquid simultaneously with its oxygenation in oxygenators 230. Carbon dioxide typically is generated by respring cells in reactors 200. Obviously, in the broad practice of the present invention any of a wide variety of normally gaseous constituents may be added to, or removed from the recirculating liquid by properly selecting the membrane material with this arrangement and this aspect of the present invention need not be limited solely to aerobic processes.

In the arrangement illustrated in FIG. 5, the liquid to be oxygenated is flowed through the tubes of the gas membrane exchanger and the oxygen-containing gas, normally comprising air, enriched air or oxygen, is flowed through the exchanger on the shell side. If one desires to enhance the rate of mass transfer, generally oxygen is used at an elevated pressure, for example, up to about 10 atmosphere absolute pressure or higher. The liquid is passed through the tubes of the gas membrane exchanger at a high Reynolds number in order to minimize fouling by cell growth on the tubes. After exiting the oxygenator, the liquid is recirculated using pumps 235 to the fluidized bed through heat exchangers 240, which adjust the temperature of the liquid to optimize conditions in reactors 200. Generally, specially selected recirculation pumps are used (such as blade-less centrifugal blood pumps, e.g., a Biomedicus pump, or flexible rotor vane pumps, e.g., Jabsco pumps) which do not damage cells entrained in the recirculating liquid. Enzyme released into the liquid as a consequence of cellular damage may degrade the desired product or other components of the culture liquid. Prior to being introduced into the reactor, the recirculated liquid may be further treated (e.g., by adding reagents to control pH; by adding nutrients, drugs or other materials to influence the metabolism and/or growth of the cells or microorganisms in reactors 200; and by removing metabolic products and by-products, both desirable and undesirable, from the recirculating liquid by a variety of techniques including ultrafiltration, affinity absorption, adsorption and many others). For example, suitable reagents may be introduced into the reactors through lines 271 and 261. By performing such treatments in a recirculating side-stream, it is possible to maintain optimum conditions in reactors 200 under continuous, aseptic operation without injuring the fragile biocatalyst beads or the immobilized bioactive material.

The recirculation rate needed in any cell culture application is a function of many variables including, inter alia, the targeted solids (biocatalyst bead) concentration during fluidization; the density of the bioactive material, i.e., the concentration of organisms, e.g., mammalian cells such as hybridomas, immobilized on or inside of the biocatalyst beads; the nature of the bioactive material (e.g., its oxygen demand), the morphology of immobilization (i.e., whether the bioactive material is contained on or in the bead matrix), the nature of the biocatalyst beads, e.g., the size of the beads and their specific gravity, the nature of the culture medium (e.g., its chemical characteristics and oxygen carrying capacity), and the nature of the treatment to be performed on the recirculating liquid.

Typically, in order to maximize efficiency the cell culture process is operated under fluidization conditions that yield a fluidized bed void volume within the range of about 60% to about 75%. The void packing density of a packed bed of typical biocatalyst beads is about 50%-60%. Operation at a fluidized bed void volume of lower than about 60% gives insufficient mixing between the biocatalyst beads and culture medium resulting in poor mass transfer, while operation at a fluidized bed void volume of above about 75% constitutes an inefficient usage of the reactor volume and impedes the natural disengagement of beads from the recirculating liquid at the effluent or outflow end of the fluidized bed. Preferably, the fluidization conditions are adjusted to give a fluidized bed void volume of about 60% to about 70%, depending upon the rate of mass and energy transfer needed, the bead attrition rate, etc.

The recirculation rate also is influenced by the concentration and nature of the cells or microorganisms in the biocatalyst beads. For example, for any specific oxygen-consuming microorganism, as the concentration (density) of the microorganisms inside the biocatalyst beads increases, higher recirculation rates are required in order to maintain adequate oxygen and/or nutrient transfer in the fluidized bed. Additionally, certain microorganisms, such as bacteria, generally have very high specific oxygen demands, and therefore normally will require higher recirculation rates and smaller, denser beads to maintain proper operating conditions than certain other organisms such as eukaryotes and mammalian cells which have much lower specific oxygen demands. For example, while *Escherichia coli* typically requires about 0.1 mmol $O_2$ per g-cell per minute, *Penicillium chrysogenum* generally requires only about 0.02 mmol $O_2$ per g-cell per minute and a typical hybridoma mammalian cell may require only about $5 \times 10^{-7}$ mmol $O_2$ per $10^6$ cells per minute.

The properties of the biocatalyst beads, particularly bead size and specific gravity, also influence the necessary recirculation rate. While suitable bead sizes will be influenced by the particular cell culture process and reactor design, beads having a particle size within the range of about 100 $\mu$m to about 1000 $\mu$m generally have proven to be suitable. Bead specific gravities between about 1.05 and 2.0 also have been investigated and found to be suitable depending upon the circumstances. Generally, beads having higher specific gravities within this range may be preferred since a higher specific gravity permits a higher recirculation rate and a higher reactor aspect ratio. At higher reactor aspect ratios (the aspect ratio is a quotient of the height of the reactor to its diameter) the fluidized bed reactor is less likely to encounter fluid distribution problems such as short circuiting. The preferred fluidized bed depth for production systems is about two meters.

Figure 7:
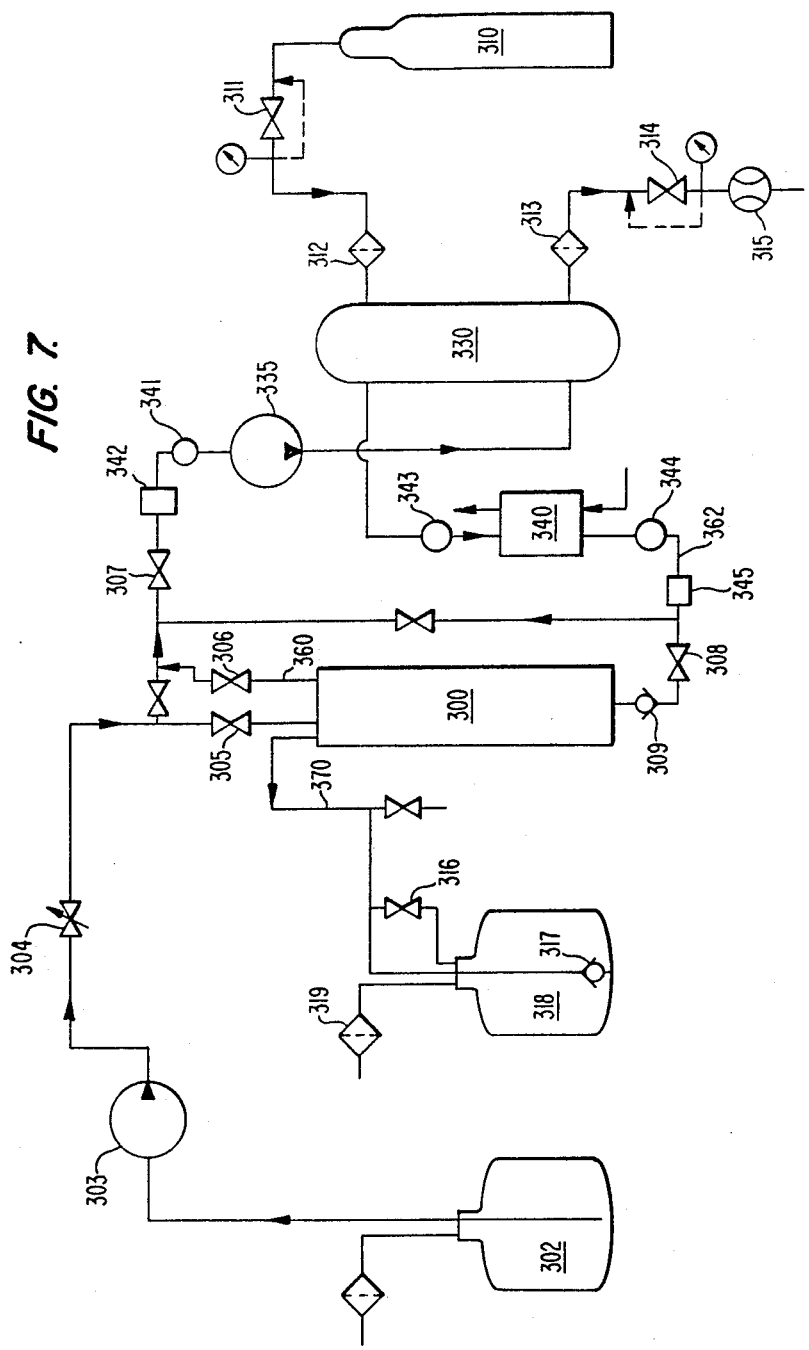
FIG. 7 is a schematic flow sheet of apparatus useful for practicing continuous aerobic cell cultivation in accordance with the invention.

Referring next to FIG. 7, a schematic flow diagram of a cell culture process and apparatus suitable, for example, for continuously manufacturing antibody in accordance with this invention is shown. Biocatalyst beads containing immobilized hybridomas manufactured for example by the procedure in the above-noted copending application are particularly suited for this process. A thick slurry of such biocatalyst beads is suspended and agitated in fluidized bed 300, for example, of the type illustrated above in FIG. 5. The cell concentration inside such biocatalyst beads typically is about $10^8$ cells per mm of beads for hybridomas of a 14 $\mu m$ diameter. During fluidization, the liquid surrounding the beads typically contains a concentration of organisms of about 1/10th that value. At fluidizing conditions (i.e., average bed void volume of about 60%) the average cell concentration in the bioreactor volume is about 40% of the concentration in the beads themselves. In other words, the actual reactor cell concentration (beads and liquor together) is approximately $4.6 \times 10^7$ cells per mm.

As shown in FIG. 7, fresh nutrient medium is fed to a fluidized bed bioreactor 300 from a medium storage vessel 302 through pump 303 and valves 304 and 305. A liquid stream 360 is separated from the top of the bioreactor 300 to form a recirculating culture liquor. The culture liquor is circulated outside the fluidized bed through line 360 and valves 306 and 307 and pump 335 in order to appropriately treat the culture liquor in separate treatment means, which liquid then is returned to the bottom of the bioreactor through line 362 and valves 308 and 309 to produce the fluidization action in bioreactor 300. While only a single recirculating stream and associated equipment is illustrated in FIG. 7, it should be emphasized that in actual practice parallel circuits generally will be provided to permit easy isolation of such equipment for maintenance and repair without jeopardizing the aseptic integrity of the system. This ease of maintaining aseptic operation is a particularly preferred feature of the present invention. A heat exchanger 340 also is inserted in the recirculation loop in order to adjust the temperature of the recirculating liquor and thereby control the temperature in bioreactor 300 at its optimum condition.

Oxygen is transferred to this recirculated liquid and $CO_2$ is removed therefrom by a membrane gas exchanger 330. The culture liquid is flowed through the membrane gas exchanger 330 in counter-current flow with a stream of air or enriched oxygen, preferably pressurized, delivered from oxygen storage tank 310 through control valve 311 and filter 312. Waste gas containing $CO_2$ is discharged through filter 313, valve 314 and flow meter 315.

As noted, an external heat exchanger 340 controls the temperature of the recirculating culture liquor and hence the bioreactor temperature. Instrumentation and sensors, such as a pH probe 341, a dissolved oxygen probe 342, temperature sensors 343 and 344, and a turbidity probe 345, are installed in the external recycle loop for easy access and calibration.

In this arrangement, the recycle dilution rate can be adjusted independently of the feed dilution rate in order to control each separately to achieve optimum performance in reactor 300. For example, the recycle dilution rate (the quotient of the volumetric recycle flow rate and the reactor volume), which normally is the major fluidizing flow, can be very high, e.g., up to about 1000 $hr^{-1}$, while the feed dilution rate or fresh nutrient medium throughflow dilution rate (the quotient of the volumetric flow rate of fresh nutrient medium and the total reactor system volume) can, at the same time, be very low, e.g., down to about 0.006 $hr^{-1}$. A dilution rate between 0.1 to 0.4 $hour^{-1}$ typically is used for culturing hybridomas which have a maximum specific growth rate of about 0.04 $hour^{-1}$. For a ten liter reactor used to culture hybridomas, a recycle dilution rate of 150 $hr^{-1}$ or less generally will be suitable. Separation of the recirculating and the feed or throughflow dilution rates is a very convenient and advantageous feature of the present invention.

The present method for continuously culturing cells is similar to the operation of a chemostat in so far as spent nutrient medium or harvest liquor continuously flows out of the reactor (through line 370 in FIG. 7) at the same rate that fresh nutrient medium is pumped into the reactor. The harvest liquor carries with it freely-suspended cells at a concentration equal to the free-cell concentration in the reactor. Because of this feature, the operation of a chemostat depends on continuous cell reproduction in the reactor, at a rate, under steady state conditions, equal to the fresh nutrient throughflow dilution rate. Accommodation of an increased cell cycle time (doubling time) in a chemostat, thus requires a lowering of the feed dilution rate. At the other end of the spectrum, the maximum possible dilution rates for a chemostat is limited by the phenomenon of washout. Washout is the elution or removal of all cells from a reactor via the harvest stream. Washout occurs when the feed or fresh nutrient dilution rate exceeds the maximum specific cell growth rate of the cell or microorganism being cultured. More simply stated, washout occurs when the residence time of the nutrient medium is less than the cells' minimum cycle time. The method of the present invention avoids these limitations, inherent in the operation of a chemostat, because over 90% and up to 95% to 99% of the cell population is immobilized in the beads. The concentration of this immobilized population is substantially uninfluenced by changes in the feed dilution rate. In fact, as is described more fully in the examples that follow, the method of the present invention is operated at a feed or throughflow dilution rate, which if used in a chemostat of equal volume, would lead to a washout condition.

A typical optimum dilution rate for growing hybridomas in a chemostat is about 0.01 to 0.02 $hr^{-1}$-note that hybridomas typically have maximum specific growth rates of less than about 0.07 $hour^{-1}$. This feed dilution rate should be contrasted with the typical dilution rate value of 0.1 $hr^{-1}$ used in the present method for culturing hybridomas (see Example 3). Since the dilution rate used in the present invention is 5 to 10 times higher than the dilution rates used in a chemostat, a reactor subjected to a change in operation is able to reattain steady state conditions much more quickly if operated in accordance with the method of the present invention than if operated as a chemostat.

A product stream of harvest liquor is removed from the bioreactor through line 370 and valves 316 and 317, is passed through an in-line microporous filter 321 to remove cells and cell debris and is collected in storage vessel 318. Thereafter, the liquid is removed from vessel 318 and the antibodies can be separated and recovered by first removing additional cells and cell debris from the harvest liquor, with a microporous filter, filter 319, followed by removal of about 95% of the water by tangential-flow ultrafiltration. An ion-exchange chromotography column may then be employed to extract bovine serum albumin or other constituents of the recovered liquid if present in the culture medium. The column is followed by one or more steps of high pressure liquid chromatography for final purification before filter sterilization and lyophilization, or the bottling of a sterile-liquid product containing the recovered antibody.

In addition to products comprising primary and secondary metabolites of the cell culture, the product may also comprise the cellular material or biomass itself. For example, genetically engineered E. coli with an rDNA product that is not expressed, e.g., insulin, could be cultivated in and recovered from reactor 300. With certain materials for the biocatalyst beads, e.g., porous or fibrous structures as described in the above-noted copending application, excess cells from an expanding cellular colony are expelled directly through the outer pores of the fibrous beads without rupturing the bead structure, thereby permitting the desired cell product to be recovered as an entrained component of the culture medium. In the practice of the present invention, other methods for recovering the biomass directly from the biocatalyst beads themselves also can be employed and the present invention is not intended to be limited to any particular embodiment.

The present method is particularly useful for cultivating microorganisms or cells which have been altered genetically or which have been genetically selected for increased production, for example, of a target protein. Such genetically altered or high productivity microorganisms and cells often exhibit genetic instability. In chemostat cultures of hybridomas, for example, genetic degenerations leading to a significant decline in productivity have been observed to occur after 40 to 50 generations. Similar declines have not been observed in hybridomas cultured according to the method of the present intention (Example 3).

Although not wishing to be bound to any particular theory, applicants believe that operation of the present invention at a high feed dilution rate, i.e. (fresh nutrient dilution rate), prevents a mutant cell generated in one bead from contaminating other beads. In the present invention, before a mutant cell can contaminate an entire culture, its progeny must be expelled from one bead into the fluidizing liquid and then must enter another bead. At the high dilution rates used in the present invention, however, mutant cells expelled into the fluidizing liquid tend to be removed with the spent nutrient medium or harvest liquor before having an opportunity to contaminate other beads. Thus, mutations tend to be isolated in the bead in which they occur. Additionally, because a high rate of cellular reproduction is not necessary to continuous operation of the present method, culture conditions may be adjusted to reduce reproduction, particularly when working with cells that produce non-growth-associated products. Applicants have found that operation at conditions favoring a low rate of cell reproduction further tend to extend the genetic life of highly productive cultures.

The following examples are intended to more fully illustrate the invention without acting as a limitation on its scope.

EXAMPLE 1

A fluidizing bed reactor of the configuration shown in FIG. 1 may have an internal base diameter of 0.86 meters and a height of 2.0 meters. The capacity of this reactor may be about 1000 liters. The propeller should have a tip diameter of about 0.86 meters and a hub diameter to tip diameter ratio of about 0.5. The propeller tip speed during fluidization should be between 1.2 and 2.4 m/sec. The biocatalyst beads can be formed from a hydrocolloid matrix weighted with a mineral (i.e., kappa-carrageenan with silica powder) and can contain immobilized therein live yeast cells of *Saccharomyces cerevisiae* (from PEDCO International—M-4 molasses strain). The nutrient medium (substrate) for feeding to the reactor can be predominantly glucose with trace amounts of other nutrients normally employed in this type of fermentation reaction (anaerobic). The medium from the top of the reaction zone would be partially recovered continuously to give an average yield of about 50 kg/hr of ethanol.

EXAMPLE 2

A fluidized bed bioreactor was constructed having a diameter of 2 inches and a height of about 8 inches. The capacity of this reactor is about 400 mm. Biocatalyst beads were formed from a hydrocolloid matrix weighted with a mineral, i.e., K-carrageeman weighted with silica powder. The beads had live recombinant yeasts cells of *S. cerevisiae*, obtained from Integrated Genetics of Framingham, Mass., immobilized therein. These cells had a minimum cycle time (doubling time) within the range of 1.5 to 6 hours, corresponding to a maximum specific cell growth rate within the range of 0.12 to 0.46 hour$^{-1}$. A nutrient medium, also obtained from Integrated Genetics, containing glucose and other nutrients normally employed in this type of aerobic fermentation process, was pumped to the bioreactor at a rate sufficient to yield a residence time (based on the feed rate) of about 2 hours. This corresponds to a feed dilution rate of 0.5 hour$^{-1}$. As a consequence, the feed dilution rate inherently exceeded the maximum specific growth rate of the cultured microorganisms in this process. The bed of biocatalyst beads was fluidized by recirculating the fermentor (culture) liquor, using a magnetically coupled gear pump, at a rate sufficient to yield a recycle residence time of less than about one minute in the reactor. In order to oxygenate the bioreactor, the recirculation liquid was passed through a silicone membrane oxygenator manufactured by SciMed Co., Minneapolis, Minn. High purity oxygen gas was used as the oxygen source. Carbon dioxide was removed through the silicone membrane simultaneously with oxygenation. The recirculation liquid was introduced into the bioreactor through a nozzle similar in design to FIG. 6.

The above-described bioreactor was operated continuously for more than 1000 hours producing a product stream containing approximately 100 nanograms per milliliter of alpha human chorionic gonadatropin (α-HCG). A batch reactor operated under similar conditions produced product at a rate about 20 times lower.

EXAMPLE 3

A ten liter capacity fluidized bed bioreactor similar in construction to one stage of the configuration shown in FIG. 5 may be constructed having an internal diameter of about 4 inches and a height from the distribution plate to the effluent line of about 5 feet. The distributor plate will be provided with a horizontal flow-directing nozzle of the design illustrated in FIG. 6. The nozzle will have twelve approximately one-eighth inch diameter holes equally spaced about its circumference located 0.5 inch above the surface of the distribution plate. A bed of glass pebbles three inches deep also may be supported by the distribution plate.

The bioreactor can contain about four liters of biocatalyst beads formed from a weighted fibrous polymer (i.e., collagen with silica powder) containing immobilized mammalian cells (hybridoma VX-7). These cells have a minimum cycle time (doubling time) of about 14 hours, corresponding to a maximum specific cell growth rate of about 0.049 hour$^{-1}$. The beads will have an average diameter of about 1000$\mu$, a specific gravity of about 1.15 and the cell density within the beads can be about $7 \times 10^7$ cells/mm.

The biocatalyst beads will be fluidized by recirculating the culture medium in the reactor at a flow rate of about 2 liters per minute. Fresh nutrient medium also will be introduced into the bioreactor at a rate of about 1 liter per hour and a product stream having an equivalent flow rate will be removed.

The bioreactor will be aerated by passing the recirculating culture medium through a gas membrane oxygenator. The oxygenator will consist of a 3 liter vessel having 100 feet of a single, helically wound tube of silicon tubing (0.25 inch internal diameter) having an oxygen permeability of about $1.34 \times 10^{-6}$ mmols O$_2$-mm per cm$^2$Hg per minute. Air can be fed to the oxygenator at a rate of about 1 liter per minute and a carbon dioxide-containing gas will be discharged at a substantially equivalent rate.

The feed rate of 1 liter per hour corresponds to a feed dilution rate of between about 0.07 and 0.1 hour$^{-1}$ (1 liter per hour per 10–14 liters of total reactor system volume). This dilution rate should be compared with a typical optimum dilution rate of 0.02 hr$^{-1}$ for hybridomas grown in a chemostat at a cell concentration of about $3 \times 10^6$ total cells per milliliter. In any event, the feed dilution rate to be used in the process inherently exceeds the maximum specific growth rate of the cultured cells.

vided at the base of the fluid bed reactor. The distributor had a 2.4 mm diameter jet nozzle positioned in the orifice of the distributor.

The bioreactor was aerated by passing, recirculating culture medium through a gas membrane oxygenator. The oxygenator consisted of a vessel having about 7.6 meters of silicon tubing (Dow Silastic) having a 6.4 mm internal diameter and a 9.5 mm outer diameter, thus providing about 1520 sq. cm. of gas permeation area on the shell side. High purity oxygen gas was used as the oxygen source. Oxygenation of the recirculating culture medium was controlled to maintain the dissolved oxygen concentration in the reactor between about 40 to 60% of its air saturation value. Under certain conditions at the higher dilution rates of fluid bed operation, a high oxygen consumption rate in the reactor caused the dissolved oxygen to drop below 40%, i.e. to around 30%.

The reactor was used to culture a mammalian hybridoma cell line VX-12 at a temperature of about 37° C. and a pH of about 7.2. Cell line VX-12 produces an IgG antibody. The hybridoma was cultured using Dulbecco's Modification of Eagle's Medium (DMEM) containing fetal calf serum (FCS). Initially, the reactor was inoculated with 200 ml of an inoculum having $1.45 \times 10^6$ viable cells per milliliter and was operated in a chemostat mode as a basis for comparison with later fluidized bed operation. The maximum antibody concentration achieved at a dilution rate of 0.019 hour$^{-1}$ and with a nutrient medium of DMEM with 5.0% FCS was 35 mg/ml. The calculated chemostat productivity was 0.675 mg/l/hr.

The bioreactor then was charged with about 205 ml (wet volume) of biocatalyst beads formed from a collegen sponge weighted with stainless steel having an average diameter of about 500 m and a specific gravity of about 1.1 to 1.2. After adding the biocatalyst beads to the reactor, the dilution rate (based on total system volume) was increased gradually from 0.019 hours$^{-1}$ up to 0.240 hours$^{-1}$. A product stream having an equivalent flow rate was removed. A well-defined decrease in harvest cell concentration (concentration of free cells in suspension) was observed as the dilution rate was raised above the maximum specific cell growth rate (generally between 0.04 and 0.45 hour$^{-1}$ for hybrodoma cells).

The biocatalyst beads were fluidized by recirculating the culture medium using a Biomedicus shear pump at a flow rate of about 500 ml/min. The following table summarizes the important reactor data. As shown, much higher productivities were achieved in the fluidized bed reactor than in the chemostat mode.

TABLE

| Medium | Dilution Rate (hour$^{-1}$) | Number of Residence Times - Total System Vol. | IgG Concentration ($\mu$g/ml) | | Productivity - Based Vol. of Expanded Bed (mg/l/hr) | |
|---|---|---|---|---|---|---|
| | | | max. | aver. | max. | aver. |
| DMEM W/5% FCS | 0.143 | 34 | 34.8 ± 4.3 | 30.5 ± 3.9 | 10.6 ± 1.4 | 9.3 ± 1.2 |
| DMEM W/5% FCS | 0.190 | 36 | 56.0 ± 10.0 | 43.4 ± 5.6 | 22.8 ± 4.1 | 17.7 ± 2.3 |
| DMEM W/5% FCS | 0.240 | 69 | 50.0 ± 6.4 | 40.2 ± 4.9 | 25.1 ± 3.3 | 20.5 ± 2.5 |
| DMEM W/0.5% FCS | 0.190 | 57 | 28.0 ± 4.9 | 23.3 ± 2.9 | 13.7 ± 1.7 | 12.0 ± 1.5 |

EXAMPLE 4

A fluidized bed bioreactor system similar to that illustrated in FIG. 7 was assembled having a reactor volume of about 475 ml and a recycle loop volume (including the volume of the membrane oxygenator, heat exchanger and piping) of about 325 ml to give a total reactor system volume of about 800 ml. A fluid distributor assembly of the type illustrated in FIG. 8 was pro-

EXAMPLE 6

A 24 liter capacity fluidized bed bioreactor similar in construction to one stage of the configuration shown in FIG. 5 was constructed having an internal diameter of about 6 inches and a height from the top of the distribution device to the effluent line of about 5 feet. The distributor device was a conical distributor of the design illustrated in FIG. 8. The nozzle at the bottom of the cone had an inlet diameter of 0.875 inches and the sides sloped outwardly at an angle of 60°. the bioreactor was equipped with a gas membrane oxygenator vessel containing 40 tubes of silicon tubing (0.25 inch internal diameter and 0.031 inch wall thickness) each about 65 feet long. A mixture of nitrogen and oxygen was fed to the oxygenator at a rate of about 5 liter per minute and a carbon dioxide-containing gas was discharged at a substantially equivalent rate.

The bioreactor was charged with about 9.0 liters of biocatalyst beads formed from a weighted fibrous polymer (i.e., collagen weighted with metal) and containing immobilized mammalian cells, i.e., CHO cells genetically engineered to produce human tissue plasminogen activator (tPA). The initial viable cell density was about $1.4 \times 10^5$ cells/ml culture. These cells have a minimum cycle time (doubling time) of about 16 hours, corresponding to a maximum specific cell growth rate of about $0.043$ hour$^{-1}$. The beads had an average diameter of about 700μ, and a specific gravity of about 1.47.

The fresh culture medium feed rate was increased over about 8 days to about 270 liters/day. After about 15 days the medium feed rate was further increased to about 330 liters per day (13.75 l/hr). The biocatalyst beads were fluidized by recirculating the culture medium in the reactor at a flow rate between 6 to 11 liters per minute. A product stream having an equivalent flow rate to the medium feed rate was removed.

The medium feed rate of 13.75 liter per hour corresponds to a feed dilution rate of about $0.23$ hour$^{-1}$ based on about 60 liter of total reactor system volume. The feed dilution rate used in this process exceeds the maximum specific growth rate of the cultured cells by a factor of about 5.

Figure 11:
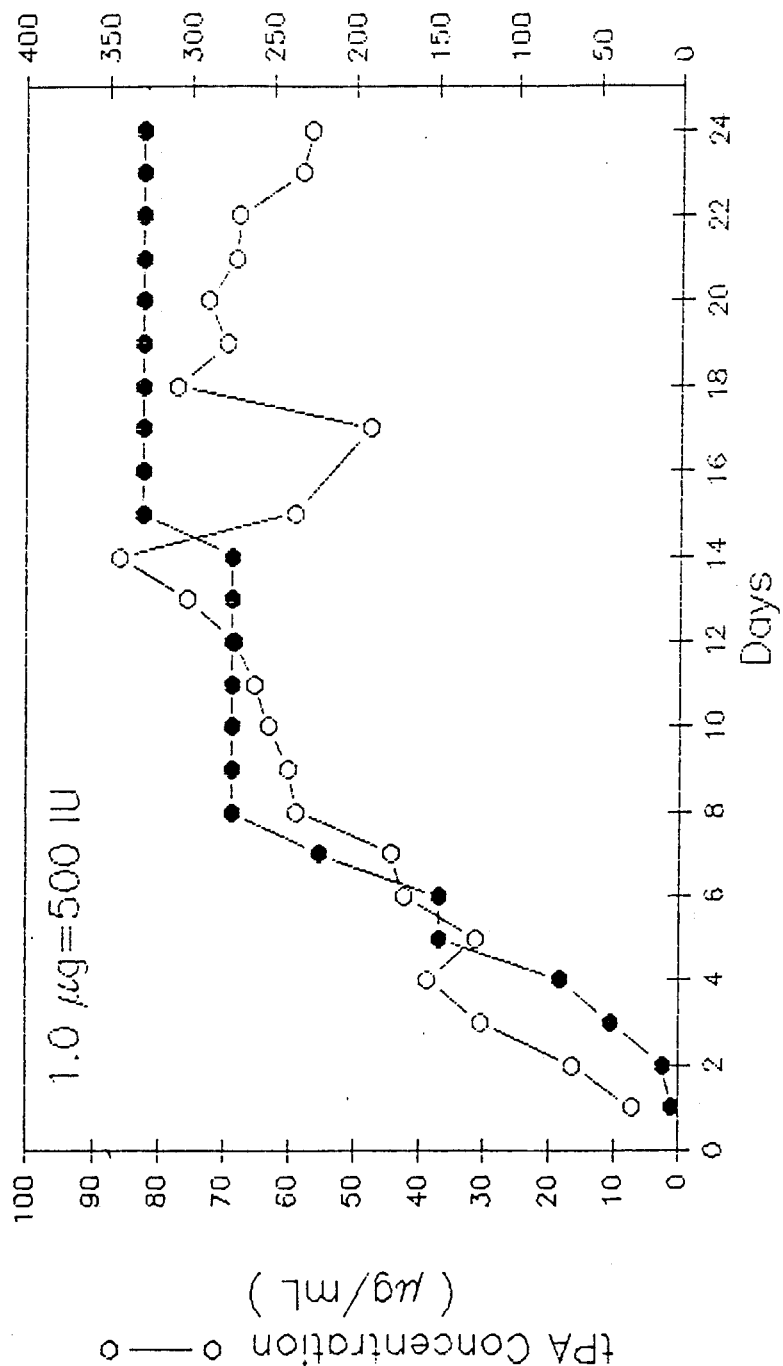
FIG. 11 is a graph showing the tPA yields achieved in the practice of the process of the present invention employing CHO cells.

The results of the test run of this Example are shown in FIG. 11. As will be seen in FIG. 11, the tPA concentration reaches a maximum after 13 days of about 87 μg/ml. The average cell specific productivity at the maximum medium feed rate (13.75l/hr) was 39.6 μg/$10^6$ cells/hr. These results are about 5 to 20 times greater than any heretofore reported results for tPA production. For example, tPA cell specific production values of 2.1 to 6.7 μg/$10^6$ cells/day have been reported (See McGraw-Hill's) Biotechnology Newswatch, Vol. VII, No. 16, p.5, Aug. 17, 1987. Moreover, the unexpected benefits of the present invention are demonstrated by culturing the same CHO cell line in conventional equipment (e.g., "Cell Factory" apparatus available from Nunc, Denmark). The highest productivity achievable with this cell line in conventional processing equipment was 7 to 10 times lower than the results achieved when using the process of the present invention.

It will be obvious to one of ordinary skill that numerous modifications may be made without departing from the true spirit and scope of the invention which is to be limited only by the appended claims.

We claim:

1. A method for continuously culturing cells comprising the steps of:
   (a) providing a reaction zone containing a bed of porous biocatalyst beads, said beads having immobilized therein microorganisms or cells;
   (b) fluidizing said bed of biocatalyst beads with a liquid nutrient medium,
   (c) separating said beads from liquid nutrient medium exiting one end of said reaction zone so that said beads remain in said reaction zone;
   (d) treating a portion of the separated liquid nutrient medium in a treatment zone, separate from the reaction zone, so as to alter the temperature or composition of the separated liquid;
   (e) recirculating said treated portion of the separated liquid nutrient medium back to said reaction zone as at least part of said liquid nutrient medium for fluidizing said bed of biocatalyst beads;
   (f) recovering another portion of said separated liquid nutrient medium as product; and
   (g) feeding fresh nutrient medium into said reaction zone at a rate equal to the recovery of separated liquid nutrient medium as product, said rate yielding a feed dilution rate above the maximum specific growth rate of said microorganisms or cells.

2. The method of claim 1 wherein said fluidizing step comprises simultaneously pumping said liquid nutrient medium and stabilizing the velocity profile of the flow of said liquid nutrient medium upwardly through said reaction zone with a stabilizing means, wherein said stabilizing means is a pump impeller located at the bottom of said reaction zone to suspend said beads above said impeller, wherein the rotation of said impeller forces said liquid nutrient medium from below said impeller upwardly into said reaction zone, and the blades of said impeller are adapted to stabilize the velocity profile of the flow of said liquid nutrient medium above the bottom of the reaction zone without any other stabilizing means above said impeller.

3. The method of claim 1 wherein said fluidizing step comprises flowing said treated and recirculated portion of the liquid nutrient medium through a distribution plate having at least one nozzle which substantially horizontally directs the flow of said liquid parallel to the surface of said plate at a velocity which stabilizes the velocity profile of the flow of said liquid nutrient medium flowing upwardly through said reaction zone.

4. The method of claim 1 wherein said beads are separated from said liquid nutrient medium using a force selected from the group consisting of gravity, centrifugal, electrical and magnetic.

5. The method of claim 4 wherein said beads are separated from said liquid nutrient medium solely by gravity.

6. The method of claim 4 wherein said separating step occurs in a rotary centrifugal separator.

7. The method of claim 1 wherein said beads are prepared from materials selected from the group consisting of natural polymers, synthetic polymers, minerals and metals.

8. The method of claim 7 wherein said beads are prepared from materials selected from the group consisting of natural polymers and synthetic polymers and said beads are weighted with an inert material to increase their specific gravity.

9. The method of claim 8 wherein said natural polymer is a polysaccharide gel.

10. The method of claim 8 wherein said natural polymer is collagen in the form of a sponge.

11. The method of claim 1 wherein said immobilized microorganisms or cells are from the group consisting of aerobic microorganisms and aerobic cells.

12. The method of claim 11 wherein said treatment zone comprises an oxygenation zone wherein the dissolved oxygen content of the separated liquid nutrient medium is increased by contacting said liquid with an oxygen containing gas.

13. The method of claim 12 wherein said oxygenation zone comprises a membrane gas exchanger.

14. The method of claim 13 wherein said aerobic cells comprise mammalian cells.

15. The method of claim 14 wherein said mammalian cells produce antibodies.

* * * * *